United States Patent [19]

Edwards

[11] Patent Number: 4,616,004
[45] Date of Patent: Oct. 7, 1986

[54] 1-IODOPROPARGYL-3,4-DISUBSTITUTED-$\Delta^2$-1,2,4-TRIAZOLIDIN-5-ONE FUNGICIDES

[75] Inventor: Laroy H. Edwards, Napa, Calif.

[73] Assignee: Chevron Research Company, San Francisco, Calif.

[21] Appl. No.: 655,484

[22] Filed: Sep. 27, 1984

[51] Int. Cl.$^4$ .................. C07D 249/12; A61K 31/41; A01N 55/00; C07F 7/10
[52] U.S. Cl. ...................................... 514/63; 514/384; 548/264; 548/110
[58] Field of Search ................ 548/264, 110; 514/384, 514/63

[56] References Cited

U.S. PATENT DOCUMENTS

| | | | |
|---|---|---|---|
| 4,055,572 | 10/1977 | Dawes et al. | 548/264 |
| 4,087,534 | 5/1978 | Ovadia et al. | 548/264 |
| 4,088,767 | 5/1978 | Shigematsu et al. | 548/264 |
| 4,098,896 | 7/1978 | Edwards | 548/264 |
| 4,120,864 | 10/1978 | Seidel et al. | 548/264 |
| 4,170,704 | 10/1979 | Brandman et al. | 546/297 |
| 4,326,878 | 4/1982 | Zinan | 548/264 |
| 4,496,551 | 1/1985 | Moberg | 514/63 |
| 4,510,136 | 4/1985 | Moberg | 514/63 |
| 4,530,922 | 7/1985 | Moberg | 514/63 |

FOREIGN PATENT DOCUMENTS 2360623  6/1974  Fed. Rep. of Germany ...... 548/264

*Primary Examiner*—Albert T. Meyers
*Assistant Examiner*—D. L. Dinner
*Attorney, Agent, or Firm*—S. R. LaPaglia; T. G. DeJonghe; S. L. Biggs

[57] ABSTRACT

Compounds of the formula:

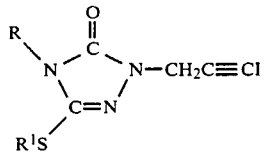

wherein R is aryl or aryl substituted with 1 to 3 substituents independently selected from halogen, lower alkyl of 1 to 4 carbon atoms, lower alkoxy of 1 to 4 carbon atoms, lower alkylthio of 1 to 4 carbon atoms, nitro, cyano, —S(O)$_n$R$^2$ wherein n is 1 or 2 and R$^2$ is lower alkyl of 1 to 4 carbon atoms; or alkyl, cycloalkyl, lower alkenyl or lower alkynyl, all optionally substituted with 1 to 3 halogen atoms; and R$^1$ is lower alkyl, trialkylsilylmethylene, aryldialkylsilylmethylene, aryl; aralkyl, or substituted aryl or aralkyl are fungicidal.

23 Claims, No Drawings

1-IODOPROPARGYL-3,4-DISUBSTITUTED-Δ²-1,2,4-TRIAZOLIDIN-5-ONE FUNGICIDES

BACKGROUND OF THE INVENTION

The present invention relates to novel 1-iodopropargyl-3,4-disubstituted-Δ²-1,2,4-triazolidine-5-one compounds which are active as fungicides.

Various compounds having a heterocyclic ring with an iodopropargyl-containing substituent have been disclosed. See, e.g., German Offenlegungsschrift No. 3,241,265, British Pat. No. 1,443,753, U.S. Pat. No. 4,170,704, and German Offenlegungsschrift No. 2,259,784.

Commonly-assigned U.S. patent application Ser. No. 629,657 discloses fungicidal N-(1-iodopropargyl)-thiazolidin-4-ones.

SUMMARY OF THE INVENTION

The 1-iodopropargyl-Δ²-1,2,4-triazolidin-5-one compounds of the present invention may be represented by the general formula:

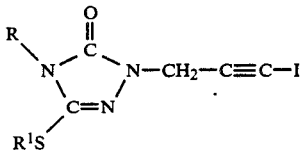

wherein R is aryl of 6 to 12 carbon atoms; substituted aryl substituted with 1 to 3 substituents independently selected from halogen, lower alkyl of 1 to 4 carbon atoms, lower alkoxy of 1 to 4 carbon atoms, lower alkylthio of 1 to 4 carbon atoms, nitro, cyano, $-S(O)_nR^2$ wherein n is 1 or 2 and $R^2$ is lower alkyl of 1 to 4 carbon atoms; or alkyl of 1 to 10 carbon atoms, cycloalkyl of 3 to 8 carbon atoms, lower alkenyl of 2 to 6 carbon atoms, or lower alkynyl of 2 to 6 carbon atoms, all optionally substituted with 1 to 3 halogen atoms; and $R^1$ is lower alkyl of 1 to 6 carbon atoms, trialkylsilylmethylene of 4 to 10 carbon atoms, aryldialkylsilylmethylene of 10 to 17 carbon atoms, aryl of 6 to 10 carbon atoms, aralkyl of 7 to 12 carbon atoms, or substituted aryl or substituted aralkyl each substituted with 1 to 3 substituents, independently selected from halogen, lower alkyl of 1 to 4 carbon atoms, lower alkoxy of 1 to 4 carbon atoms nitro, cyano, trihalomethyl, lower carbalkoxy or $-S(O)_nR^2$.

Among other factors, the present invention is based upon my finding that the compounds of this invention are surprisingly active as fungicides. In particular, these compounds are useful in combatting certain plant fungal diseases, such as downy mildews caused by organisms, such as *Plasmopara viticola* and late blights, such as that caused by *Phytophthora infestans.*

Preferred R groups include phenyl, methyl, allyl, butyl and the like.

Preferred halogens include chlorine.

Preferred $R^1$ groups include trialkylsilylmethylene, methyl, benzyl and the like.

Particularly preferred R groups include phenyl and methyl.

Particularly preferred $R^1$ groups include trimethylsilylmethylene.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group $-(CH_2)_m-$ wherein m is an integer greater than zero. Typical alkylene groups include, methylene, ethylene, propylene and the like.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkylthioalkylene" refers to an alkyl group substituted with an alkylthio group. The term "lower alkylthioalkylene" refers to groups having up to a total of 8 carbon atoms and includes, for example, ethylthiomethylene, methylthiomethylene, 2-methylthiopropylene, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkylene" refers to an alkyl group substituted with an alkoxy group. The term "lower alkoxyalkylene" refers to groups having up to a total of 8 carbon atoms and includes, for example, ethoxymethylene, methoxymethylene, 2-methoxypropylene, and the like.

The term "alkenyl" refers to unsaturated alkyl groups having a double bond [e.g., $CH_3CH=CH(CH_2)_2$] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methylpent-4-enyl, and the like.

The term "halo" or "halogen" refers to the groups fluoro, chloro, bromo and iodo.

The term "haloalkenyl" refers to alkenyl groups substituted with from 1 to 2 halogen atoms. "Lower haloalkenyl" refers to groups having a total of from 3 to 5 carbon atoms, and includes, for example, 1-chloropropenyl, 2,3-dibromo-but-3-enyl, and the like.

The term "alkynyl" refers to unsaturated alkyl groups having a triple bond (e.g., $CH_3CH\equiv CCH_2CH_3$) and includes both straight- and branched-chain alkynyl groups. "Lower alkynyl" refers to groups having a total of from 3 to 5 carbon atoms. Typical lower alkynyl groups include propynyl, butynyl, and the like.

The term "carbalkoxy" refers to the group

where R' is an alkyl group. The term "lower carbalkoxy" refers to carbalkoxy groups where R' is a lower alkyl group, and includes, for example, carbomethoxy, carboethoxy and the like.

The term "hydroxy alkyl" refers to the group —R"—OH wherein R" is branched or unbranched alkylene and the hydroxy can be on a primary, secondary or a tertiary carbon. Examples include hydroxy ethyl and 2-hydroxypropyl and 2-hydroxy-2-methyl butyl.

The term "aryl" refers to aryl groups having from 6 to 10 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 10 carbons and includes, for example, benzyl, p-chlorobenzyl, p-methylbenzyl and 2-phenylethyl.

The term "arylthio" refers to the group R'''S— wherein R''' is an aryl group; examples include phenylthio, naphthylthio, and the like.

The term "arylthioalkyl" refers to an alkyl group of 1 to 4 carbon atoms substituted with an arylthio group and includes, for example, phenylthiomethylene, naphthylthiomethylene, phenylthioethylene, and the like.

The term "alkylamino" refers to the group R'R"N— wherein R' is alkyl and R" is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "trialkylsilylmethylene" refers to the group (R')$_3$Si—CH$_2$— where R' is alkyl and each R' can be the same or different, and includes groups such as trimethylsilylmethylene, tert-butyldimethylsilylmethylene and the like.

The term "aryldialkylsilylmethylene" refers to the group:

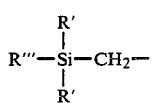

where R' is alkyl and each R' can be the same or different, and R''' is aryl, including groups, such as phenyldimethylsilylmethylene and the like.

The term "Δ$^2$-triazolidin-5-one" refers to the group:

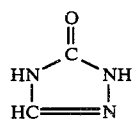

which has the conventional numbering system:

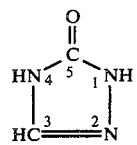

DETAILED DESCRIPTION OF THE INVENTION

The compounds of the present invention may be conveniently prepared according to the following reaction scheme:

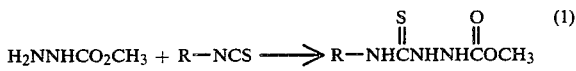

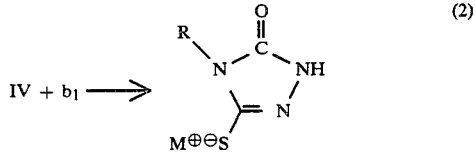

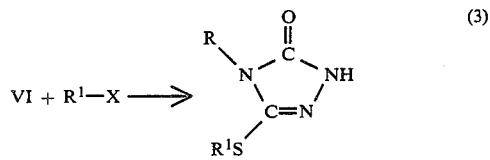

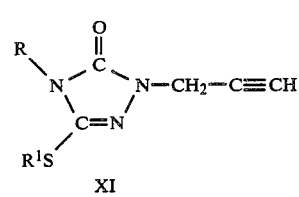

wherein R and R$^1$ are as previously defined in conjunction with Formula I; X is halogen; b$_1$, b$_2$ and b$_3$ are bases and M is an alkali metal.

Reaction (1) is conducted by combining approximately equimolar amounts of II and III in solvent. Although the reactants may be combined in any order, it is preferred to slowly add III in solvent to a mixture of II in solvent, to reduce exothermicity. Suitable solvents include inert organic solvents, such as methylene chloride, ether, dimethoxyethane, dimethylformamide, and the like. The reaction is conducted at a temperature of about 0° C. to about 50° C. or, for convenience, at reflux. The reaction is generally complete within about 3 to about 5 hours. The product, IV, is isolated by conventional procedures such as filtration, vacuum filtration, and the like.

Reaction (2) is a cyclization reaction to give the $\Delta^2$-1,2,4-triazolidin-5-one ring and is conducted by combining IV and V in solvent. Suitable bases $b_1$ include inorganic bases, such as potassium carbonate, sodium hydroxide and the like or organic bases, such as 2,6-lutidine. Approximately one equivalent base V is used per equivalent IV. Suitable solvents include low molecular weight alcohols, such as methanol, ethanol, and isopropyl alcohol, and water. The reaction is conducted at a temperature of about 50° C. to about 100° C., preferably from about 65° C. to about 80° C. or at reflux, and is generally complete within about 3 to about 6 hours. The product, VI, is isolated by conventional procedures or preferably is used in Reaction (3) as is, that is, in solvent without further isolation.

Reaction (3) is conducted by combining approximately equimolar amounts of VI and VII in solvent. Since VI is preferably prepared in situ, according to Reaction (2) and used in Reaction (3) without isolation, it is preferred to add VII in solvent to VI. If VI has been prepared in situ, VII in a small amount of solvent is dropped in to the reaction mixture from Reaction (2). Suitable solvents include organic solvents such as low molecular weight alcohols like methanol, ethanol, and isopropanol. The reaction is conducted at a temperature of from about 25° C. to about 100° C., preferably from about 65° C. to about 80° C., or at reflux. The reaction is generally complete within about 2 to about 4 hrs. The product VIII is isolated by conventional procedures, such as washing, extraction, filtration, stripping, and the like.

Reaction (4) is conducted by adding IX to a mixture of VII and X in solvent. It is preferred to first add VIII to a mixture of X in solvent. The reaction is conducted at a temperature of about 25° C. to about 100° C., preferably from about 65° C. to about 80° C. or at reflux. The reaction is generally complete within about 4 to about 6 hours. Preferably, approximately equimolar amounts of VIII, IX and X are used. Suitable bases $b_1$ include relatively strong bases such as potassium carbonate, sodium hydride, alkyl lithium salts, potassium t-butoxide, and the like. Suitable solvents include organic solvents such as low molecular weight alcohols, such as ethanol, dimethoxyethane, ether, furan, dimethylformamide, and the like. Propargyl bromide is the preferred propargyl halide XI. The product XI is isolated by conventional procedures such as extraction, stripping, chromatography, crystallization, and the like.

Reaction (5) is conducted by adding XII to a mixture of XI and XIII in solvent. It is preferred to first add XI to a mixture of XIII in solvent. It is preferable to cool the reaction mixture to about 0° C. during the addition of XII and to maintain its temperature at about 0° C. for about one hour after the addition is complete. The reaction is conducted at a temperature of about 0° to about 25° C., and is generally complete within about 1 to about 12 hours. The progress of the reaction may be conveniently monitored by watching for a color change in the reaction mixture from black (immediately after the addition of XII) to light yellow. Suitable bases $b_3$ include alkali metal alkoxides, such as sodium methoxide. Such alkoxides may be conveniently prepared in situ by adding alkali metal to alcohol which may then also act as solvent. Suitable alcohols include those having up to 4 carbon atoms such as methanol, ethanol, tert-butanol, and the like. The product I is isolated by conventional procedures such as extraction, washing, stripping, chromatography, hard-topping, crystallization, and the like.

Utility

The compounds of the present invention are useful in controlling a wide variety of pests.

These compounds are active as fungicides and are particularly effective in controlling a variety fungi which are deleterious to plants, including plant fungal infections. These compounds are particularly effective in controlling leaf blights caused by organisms such as *Phytophthora infestans* and *Septoria apii*. However, some of the compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to about 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 1-Methylcarboxy-4-phenyl-thiosemicarbazide

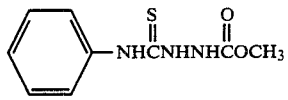

To a stirred mixture of 20 g (0.2, 0.22 mole) methylhydrazinocarboxylate in 150 ml, 27 g (0.2 mole) phenylthiocyanate was added dropwise. The reaction mixture was refluxed at about 40° C. for 3 hours and then was stirred at ambient temperature over the weekend (about 72 hours). The reaction mixture was refluxed an additional 6.5 hours; it was then cooled, vacuum filtered and dried to give 31.93 g of the above-identified product, as a solid.

EXAMPLE 2

Preparation of 4-Phenyl-3-[(trimethyl)silyl]methylthio-$\Delta^2$-triazolidin-5-one

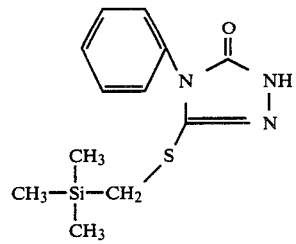

(a) To a stirred mixture of 20 g (0.09 mole) 1-methylcarboxy-4-phenyl-thiosemicarbazide (the product of Example 1) in 200 ml methanol, 6.2 g (0.045 mole) potassium carbonate were added. The reaction mixture was refluxed at about 60°–65° C. for 1 hour and then was cooled. The product, the $\Delta^2$-triazol-din-5-one-3-sulfide salt, was used in step (b) without further isolation.

(b) To the stirred mixture of the salt from step (a), 11.04 g (0.09 mole) chloromethyl trimethylsilane in 25 ml methanol was added dropwise. The reaction mixture was stirred overnight at ambient temperature, was refluxed at about 60°–65° C. for 8 hours, was allowed stirred overnight at ambient temperature, and was then refluxed an additional 2 hours. The reaction mixture was cooled, and vacuum filtered, and the solids were dried. The methanol was stripped from the filtrate; the resulting precipitate was washed with ether to give the above-identified product.

EXAMPLE 3

Preparation of 4-Phenyl-1-propargyl-3-[(trimethyl)silyl]methylthio-$\Delta^2$-triazolidin-5-one

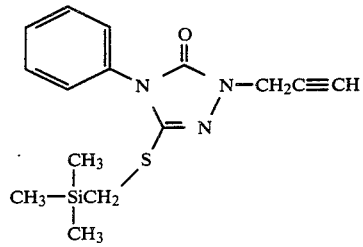

To a stirred solution of 9.2 g (0.03 mole) 4-phenyl-3-[(methyl)silyl]methylthio-$\Delta^2$-triazolidin-5-one (the product of Example 2) in 200 ml ethanol, 4.5 g (0.03 mole) propargyl bromide (80% in toluene) and 2 g (0.015 mole) potassium carbonate were added. The reaction mixture was refluxed for 6 hours, allowed to stir overnight at ambient temperature, and refluxed for an additional 3.5 hours. The reaction mixture was vacuum filtered, the solids were dried, and the filtrate was stripped to remove ethanol. The combined precipitate and residue were washed with water, extracted with methylene chloride, dried over magnesium sulfate, and stripped. The residue was washed with hexane to give the above-identified product as a light yellow solid, melting point 72°–74° C.

Elemental analysis for $C_{15}H_{19}N_3OSSi$ showed: calculated %C 56.75 %H 6.03, and %N 13.24; found %C 57.15, %H 5.77, and %N 13.63.

EXAMPLE 4

Preparation of 1-(3-iodopropargy)-4-Phenyl-3-[(trimethyl)silyl]methylthio-$\Delta^2$-triazolidin-5-one

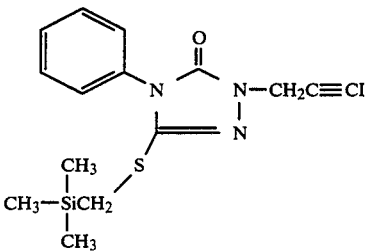

A stirred mixture of 0.23 g (0.01 mole) sodium metal in 200 ml methanol was cooled with ice, then 3.5 g (0.01 mole) 4-phenyl-1-propargyl-3-[(trimethyl)silyl]methylthio-$\Delta^2$-triazolidin-5-one (the product of Example 3) and 1.3 g (0.005 mole) iodine were added. The reaction mixture was stirred for one hour. The mixture was poured into water, washed and then extracted three times with methylene chloride. The combined methylene chloride extracts were washed twice with sodium metabisulfite, dried and stripped.

The reaction was repeated with an additional 2.6 g (0.01 mole) iodine. The reaction mixture was washed twice with water, was extracted with methylene chloride, was washed twice with concentrated sodium metabisulfite, extracted, dried and stripped to give the above-identified product.

Elemental analysis for $C_{15}H_{18}N_3OSSi$ I showed: calculated %C 40.7, %H 4.09, and %N 9.5: found %C 41.78, %H 4.48, and %N 9.7.

EXAMPLE 5

Preparation of 1-Methylcarboxy-4-methyl-thiosemicarbazide

To a stirred mixture of 20 g (0.22, 0.2 mole) methyl hydrazinocarboxylate in 150 ml methylene chloride, 14.6 g (0.2 mole) methyl isothiocyanate in 50 ml methylene chloride was added dropwise. The reaction mixture was refluxed at about 40° C. for 0.5 hour, was allowed to stir overnight at ambient temperature, and was refluxed an additional 2 hours. The reaction mixture was cooled, vacuum filtered and the solids were dried to give 27.2 g of the above-identified product.

EXAMPLE 6

Preparation of 4-Methyl-3-[2(trimethyl)-silyl]methylthio-$\Delta^2$-triazolidin-5-one

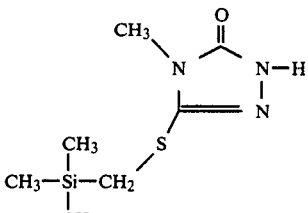

(a) To a stirred mixture of 20 g (0.1, 0.12 mole) 1-methylcarboxy-4-methyl-thiosemicarbazide (the product of Example 5) in 200 ml methanol, 6.9 g (0.05 mole) potassium carbonate was added. The resulting mixture was refluxed at about 60°–65° C. for 2 hours and then cooled. The resulting $\Delta^2$-thiazolidin-5-one sulfide salt, was used in step (b) without further purification.

(b) To the stirred mixture of the salt from step (a), 12.3 g (0.1 mole) chloromethyltrimethylsilane in 25 ml methanol was added dropwise. The reaction mixture was stirred overnight at ambient temperature, was refluxed at about 60°–65° C. for 8 hours, was stirred overnight at ambient temperature and was refluxed an additional 2 hours. The reaction mixture was cooled and vacuum filtered, the solids were dried, and the filtrate stripped to remove methanol. The solids were combined and then washed with water, extracted with methylene chloride, dried and stripped to give the above-identified product.

EXAMPLE 7

Preparation of 4-methyl-1-propargyl-3-[(trimethyl)silyl]methylthio-$\Delta^2$-triazolidin-5-one

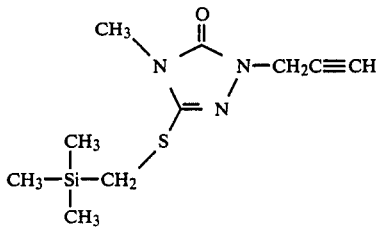

To a stirred solution of 5.2 g (0.03 mole) 4-methyl-3-[(trimethyl)silyl]methylthio-$\Delta^2$-triazolidin-5-one (the product of Example 6) in 200 ml ethanol, 4.5 g (0.03 mole) propargyl bromide 80% in toluene, and 2 g (0.015 mole) potassium carbonate were added. The reaction mixture was refluxed for 6 hours, stirred overnight at ambient temperature, and refluxed for an additional 5 hours. The reaction mixture was vacuum filtered, the solids were dried and the filtrate was stripped to remove ethanol. The solids were combined, washed with water, dried over magnesium sulfate and stripped to give the above-identified product as an amber oil.

Elemental analysis for $C_{10}H_{17}N_3OSSi$ showed: calculated %C 47.02, %H 6.71, and %N 16.45; found %C 47.52, %H 7.38, and %N 16.15.

EXAMPLE 8

Preparation of 1-(3-iodopropargyl)-4-methyl-3-[(trimethyl)silyl]methylthio-Δ²-triazolidin-5-one

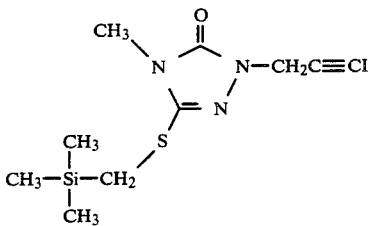

A stirred mixture of 0.2 g (0.008 mole) sodium metal in 200 ml methanol was cooled with ice, then 2 g (0.008 mole) 4-methyl-1-propargyl-3-[(trimethyl)silyl]methylthio-Δ²-triazolidin-5-one (the product of Example 7) and 2 g (0.008 mole) iodine were added. The reaction mixture was stirred for 2 hours, still cooled with ice. The reaction mixture was washed with water and then extracted with methylene chloride, washed twice with concentrated sodium metabisulfite, extracted with methylene chloride, dried and stripped to give the above-identified product.

Elemental analysis for $C_{10}H_{16}OSSi$ I showed: calculated %C 34.28, %H 4.6, and %N 12; found %C 36.38, %H 5.39 and %N 10.95.

EXAMPLE 9

Preparation of 1-Methylcarboxy-4-allyl-thiosemicarbazide

Into a stirred mixture of 20 g (0.2 mole) methyl hydrazinocarboxylate in 150 ml methylene chloride, 19.8 g (0.2 mole) allyl isothiocyanate in 50 ml methylene chloride was dropped in. The reaction mixture was refluxed at about 40° C. for 3.5 hours, allowed to stir overnight at ambient temperature, refluxed about 8 hours, stirred overnight at ambient temperature, refluxed 8 hours, stirred overnight at ambient temperature, and refluxed an additional 4 hours. The reaction mixture was cooled, vacuum filtered and the solids dried. The filtrate was poured back into the flask, at which point a precipitate started to form. Hexane was added. A yellow precipitate formed which was vacuum filtered and dried to give 29.6 g of the above-identified product.

EXAMPLE 10

Preparation of 4-Allyl-3-benzylthio-Δ²-triazolidin-5-one

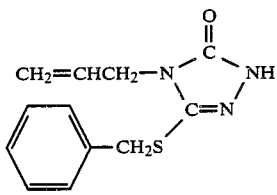

(a) A mixture of 18.8 g (0.1 mole) 1-methylcarboxy-4-allyl-thiosemicarbazide (Example 9) and 6.9 g (0.05 mole) potassium carbonate in ethanol was refluxed for two hours to give the Δ²-thiazolidin-5-one sulfide salt which was used in step (b) without further isolation.

(b) To the salt mixture from step (a), 17.1 g (0.1 mole) benzyl bromide was dropped in. The reaction mixture was stirred overnight at ambient temperature, refluxed for 8 hours and stirred overnight again at ambient temperature. The mixture was filtered. The solid was dried. The filtrate was stripped to remove ethanol. The solid and residue were each washed with water, combined, and then extracted with methylene chloride. The methylene chloride fraction was dried and stripped to give 20.65 g of the above-identified product.

EXAMPLE 11

Preparation of 4-Allyl-3-benzylthio-1-propargyl-Δ²-triazolidin-5-one

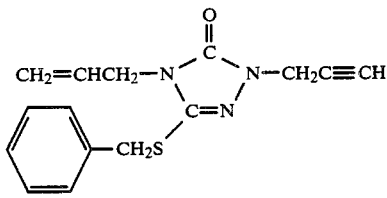

A mixture of 12 g (0.05 mole) (0.046 mole) 4-allyl-3-benzylthio-Δ²-triazolidin-5-one (the product of Example 10), 7.4 g (0.05 mole) 80% propargyl bromide in toluene and 3.5 g (0.025 mole) potassium carbonate in ethanol was stirred for two hours at ambient temperature, refluxed for 2.5 hours, stirred over the weekend (about 72 hours) at ambient temperature, refluxed for an additional 8 hours, and stirred overnight at ambient temperature. The reaction mixture was filtered. The solid was dried, and the filtrate was stripped. The solid and the residue were each washed with water combined and then extracted with methylene chloride. The methylene chloride fraction was dried over magnesium sulfate and stripped to give the above-identified product.

Elemental analysis for $C_{16}H_{15}N_3OS$ showed: calculated %C 63.1, %H 53, and %N 14.7; found %C 61.67, %H 5.43, and %N 14.7.

EXAMPLE 12

Preparation of 4-Allyl-3-benzylthio-1-(3-iodopropargyl)-Δ²-triazolidin-5-one

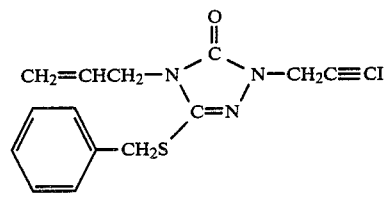

To methanol which had been placed in an apparatus dried by a heat gun through which nitrogen gas had been bubbled for about 45 minutes, about 0.24 g (0.01 mole) sodium metal was added; the resulting mixture was stirred about one hour. Then, 3 g (0.01 mole) 4-allyl-3-benzylthio-1-propargyl-Δ²-triazolidin-5-one (the product of Example 11) was added. The resulting mixture was stirred for about 30 minutes; the flask was packed in ice and then stirred an additional 30 minutes. Iodine, 2.5 g (0.01 mole) was added and the resulting mixture was stirred over the weekend. The mixture was stripped to remove methanol. The residue was washed with water and then extracted with ethyl acetate. The ethyl acetate extracts were dried over magnesium sulfate and stripped. The residue was washed with ether and stripped to give the above-identified product, as a yellow oil.

Elemental analysis for $C_{15}H_{14}IN_3OS$ showed: calculated %C 43.8, %H 3.4, and %N 10.2; found %C 46.89, %H 4.38, and %N 9.68.

Compounds made in accordance with Examples 1 to 12 are found in Table I.

In addition, by following the methods disclosed in the Detailed Description of the Invention and in Examples 1 to 12 and using the appropriate starting materials, the following compounds are made:

4-(O-chlorophenyl)-1-(3-iodopropargyl)-3-[(trimethyl)silyl]methylthio-$\Delta^2$-triazolidin-5-one;

1-(3-iodopropargyl)-4-(O-methoxyphenyl)-3-[(trimethyl)silyl]methylthio-$\Delta^2$-triazolidin-5-one;

1-(3-iodopropargyl)-4-(p-methoxyphenyl)-3-[(trimethyl)silyl]methylthio-$\Delta^2$-triazolidin-5-one;

4-allyl-1-(3-iodoproprgyl)-3-[(trimethyl)silyl]methylthio-$\Delta^2$-triazolidin-5-one;

4-(3',4'-dichlorophenyl)-1-(3-iodopropargyl)-3-[(trimethyl)silyl]methylthio-$\Delta^2$-triazolidin-5-one;

1-(3-iodopropargyl)-4-methyl-3-methylthio-$\Delta^2$-triazolidin-5-one;

1-(3-iodopropargyl)-4-isopropyl-3-trimethylthio-$\Delta^2$-triazolidin-5-one;

1-(3-iodopropargyl)-4-isopropyl-3-[(trimethyl)silyl]methylthio-$\Delta^2$-triazolidin-5-one;

4-cyclohexyl-1-(3-iodopropargyl)-3-methylthio-$\Delta^2$-triazolidin-5-one;

4-cyclohexyl-1-(3-iodopropargyl)-3-[(trimethyl)silyl]methylthio-$\Delta^2$-triazolidin-5-one;

3-benzylthio-1-(3-iodopropargyl)-4-methyl-$\Delta^2$-triazolidin-5-one;

3-benzylthio-1-(3-iodopropargyl)-4-phenyl-$\Delta^2$-triazolidin-5-one;

1-(3-iodopropargyl)-4-methyl-3-methylthio-$\Delta^2$-triazolidin-5-one;

1-(3-iodopropargyl)-4-phenyl-3-[(tertbutyldimethyl)silyl],methylthio-$\Delta^2$-triazolidin-5-one;

1-(3-iodopropargyl)-4-phenyl-3-[(phenyldimethyl)silyl]methylthio-$\Delta^2$-triazolidin-5-one;

1-(3-iodopropargyl)-4-methyl-3-[(tertbutyldimethyl)silyl]methylthio-$\Delta^2$-triazolidin-5-one;

1-(3-iodopropargyl)-4-methyl-3-[(tertbutyldimethyl)silyl]methylthio-$\Delta^2$-triazolidin-5-one;

1-(3-iodopropargyl)-4-methyl-3-[(phenyldimethyl)silyl]methylthio-$\Delta^2$-triazolidin-5-one;

4-allyl-1-(3-iodopropargyl)-3-[(tert-butyldimethyl)silyl]methylthio-$\Delta^2$-triazolidin-5-one; and 4-allyl-1-(3-iodopropargyl)-3-[(phenyldimethyl)silyl]methylthio-$\Delta^2$-triazolidin-5-one.

EXAMPLE A

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum*, *Rhizoctonia solani*, *Fusarium moniloforme*, *Botrytis cinerea*, *Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of $mg/cm^2$ needed for 99% control of the fungus ($ED_{99}$). The effectiveness of the compounds for fungicidal activity are reported in Table II in terms of the percent of the $ED_{99}$ of the test compound of the $ED_{99}$ of the standard Difolatan ®.

EXAMPLE B

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated one day later with the organism, placed in an environmental chamber and incubated at 66° F. to 68° F. and 100% relative humidity for at least 16 hours. Following the incubation, the plants were maintained in a greenhouse for approximately seven days. The percent disease control provided by a given test compound was based on the percent disease reduction relative to untreated check plants. The results are tabulated in Table II.

EXAMPLE C

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated one day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE D

Tomato Early Blight

Compounds were tested for the control of the Tomato Early Blight organism *Alternaria solani conidia*.

Tomato (variety Bonny Best) seedlings of six to seven weeks old were used. The tomato plants were sprayed with a 200-ppm solution of the test compound in an acetone-and-water solution containing a small amount of a nonionic emulsifier. The sprayed plants were inoculated one day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE E

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table II.

EXAMPLE F

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated one day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table II.

EXAMPLE G

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66° F. to 68° F. and 60% to 80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table II.

TABLE I

Compounds of the Formula

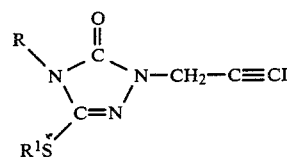

| | | | | Physical | Elemental Analysis | | | | | |
|---|---|---|---|---|---|---|---|---|---|---|
| | | | | | % C | | % H | | % N | |
| Compound | | R | R¹ | State | Calc. | Found | Calc. | Found | Calc. | Found |
| 1 | 44565 | —CH₃ | —CH₂—Si(CH₃)₃ | amber oil | 34.28 | 36.38 | 4.6 | 5.39 | 12.0 | 10.95 |
| 2 | 44564 | ⌬ | —CH₂—Si(CH₃)₃ | solid mp 132-136° C. | 40.7 | 41.78 | 4.09 | 4.48 | 9.5 | 9.7 |
| 3 | 45038 | —(CH₂)₃CH₃ | —CH₂—Si(CH₃)₃ | amber oil | 36.9 | 36.88 | 5.2 | 5.42 | 9.9 | 11.1 |
| 4 | 45149 | —CH₂CH=CH₂ | —CH₃ | yellow oil | 32.0 | 27.6 | 3.0 | 2.6 | 12.5 | 9.2 |
| 5 | 45148 | —CH₂CH=CH₂ | —CH₂—⌬ | yellow oil | 43.8 | 46.89 | 3.4 | 4.38 | 10.2 | 9.68 |

TABLE I-continued

Compounds of the Formula

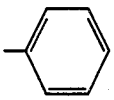

| Compound | R | R$^1$ | Physical State | %C Calc. | %C Found | %H Calc. | %H Found | %N Calc. | %N Found |
|---|---|---|---|---|---|---|---|---|---|
| 6 45043 | [phenyl] | —CH$_3$ | white solid | 38.83 | 39.9 | 2.71 | 3.01 | 11.32 | 11.62 |

TABLE II

| | | Fungicidal Activity | | | | | | | | | |
|---|---|---|---|---|---|---|---|---|---|---|---|
| | Mycelial Inhibition | | | | | | | | | | |
| Compound | Pyth. | Rhiz. | Fusar. | Botr. | Asper. | Ustil. | TLB | RB | TEB | CLB | BPM | BR |
| 1 44565 | 18 | 25 | 0 | 0 | 0 | 0 | 99 | 7 | 0 | 93 | 0 | 6 |
| 2 44564 | 18 | 13 | 0 | 0 | 0 | — | 99 | 29 | 0 | 88 | 0 | 0 |
| 3 45038 | 0 | 0 | 0 | 0 | 0 | 0 | 6 | 25 | 0 | 0 | 0 | 0 |
| 4 45149 | 25 | 43 | 0 | 0 | 64 | 0 | 99 | 81 | 88 | 79 | 0 | 0 |
| 5 45148 | 0 | 14 | 0 | 0 | 0 | 0 | 100 | 88 | 25 | 89 | 0 | 0 |
| 6 45043 | 100 | 50 | 0 | 39 | 62 | 19 | 96 | 38 | 40 | 19 | 0 | 0 |

What is claimed is:

1. A compound of the formula:

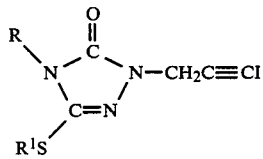

wherein R is aryl of 6 to 12 carbom atoms; substituted aryl of 6 to 12 carbon atoms substituted with 1 to 3 substituents selected from halogen, lower alkyl of 1 to 4 carbon atoms, lower alkoxy of 1 to 4 carbon atoms, lower alkylthio of 1 to 4 carbon atoms, nitro, cyano, or —S(O)$_n$R$^2$ wherein n is 1 or 2 and R$^2$ is lower alkyl of 1 to 4 carbon atoms; or alkyl of 1 to 10 carbon atoms, cycloalkyl of 3 to 8 carbon atoms, lower alkenyl of 2 to 6 carbon atoms, or lower alkynyl of 2 to 6 carbon atoms, all optionally substituted with 1 to 3 halogen atoms; and R$^1$ is lower alkyl of 1 to 6 carbon atoms, trialkylsilylmethylene of 4 to 10 carbon atoms, aryldialkylsilylmethylene of 10 to 17 carbon atoms, aryl of 6 to 10 carbons, aralkyl of 7 to 12 carbon atoms, or substituted aryl of 6 to 10 carbon atoms or substituted aralkyl of 6 to 10 carbon atoms each substituted with 1 to 3 substituents independently selected from halogen, lower alkyl of 1 to 4 carbon atoms, lower alkoxy of 1 to 4 carbon atoms nitro, cyano, trihalomethyl, lower carbalkoxy and —S(O)$_n$R$^2$.

2. A compound according to claim 1 wherein R is lower alkyl, lower alkenyl or aryl.

3. A compound according to claim 2 wherein R$^1$ is trialkylsilylmethylene, aryldialkylsilylmethylene, lower alkyl, aryl or aralkyl.

4. A compound according to claim 3 wherein R is methyl or phenyl.

5. A compound according to claim 4 wherein R$^1$ is trimethylsilylmethylene.

6. A compound according to claim 5 wherein R is methyl.

7. A compound according to claim 5 wherein R is phenyl.

8. A compound according to claim 4 wherein R$^1$ is methyl.

9. A compound according to claim 8 wherein R is phenyl.

10. A compound according to claim 1 wherein R$^1$ is trialkylsilylmethylene.

11. A compound according to claim 10 wherein R$^1$ is trimethylsilylmethylene.

12. A method of controlling fungi which comprises contacting said fungi or their plant growth environment with a fungicidally effective amount of a compound of claim 1.

13. A method of controlling fungi which comprises contacting said fungi or their plant growth environment with a fungicidally effective amount of a compound of claim 2.

14. A method of controlling fungi which comprises contacting said fungi or their plant growth environment with a fungicidally effective amount of a compound of claim 6.

15. A method of controlling fungi which comprises contacting said fungi or their plant growth environment with a fungicidally effective amount of a compound of claim 7.

16. A method of controlling fungi which comprises contacting said fungi or their plant growth environment with a fungicidally effective amount of a compound of claim 9.

17. A method of controlling fungi which comprises contacting said fungi or their plant growth environment with a fungicidally effective amount of a compound of claim 10.

18. A fungicidal composition which comprises an inert carrier and a fungicidally effective amount of a compound of claim 1.

19. A fungicidal composition which comprises an inert carrier and a fungicidally effective amount of a compound of claim 2.

20. A fungicidal composition which comprises an inert carrier and a fungicidally effective amount of a compound of claim 6.

21. A fungicidal composition which comprises an inert carrier and a fungicidally effective amount of a compound of claim 7.

22. A fungicidal composition which comprises an inert carrier and a fungicidally effective amount of a compound of claim 9.

23. A fungicidal composition which comprises an inert carrier and a fungicidally effective amount of a compound of claim 10.

* * * * *